United States Patent
Uang et al.

(10) Patent No.: US 6,639,095 B1
(45) Date of Patent: Oct. 28, 2003

(54) PROCESS FOR PREPARING OPTICALLY ACTIVE α-HYDROXY ACIDS AND DERIVATIVES THEREOF

(75) Inventors: Biing-Jiun Uang, Taipei (TW); Jia-Wen Chang, Taichung (TW); Der-Pin Jang, Hsinchu Hsien (TW)

(73) Assignee: Hardy W. Chan, San Mateo, CA (US)

( * ) Notice: Subject to any disclaimer, the term of this patent is extended or adjusted under 35 U.S.C. 154(b) by 0 days.

(21) Appl. No.: 10/148,465

(22) PCT Filed: Dec. 2, 1999

(86) PCT No.: PCT/US99/28440

§ 371 (c)(1),
(2), (4) Date: Oct. 8, 2002

(87) PCT Pub. No.: WO01/40153

PCT Pub. Date: Jun. 7, 2001

(51) Int. Cl.[7] .......................... C07C 35/22; C07C 35/24; C07C 43/30; C07C 43/32; C07C 45/00
(52) U.S. Cl. .......................... 560/55; 560/179; 560/183; 562/465; 562/529; 564/80; 568/339; 568/591; 568/820; 549/265
(58) Field of Search .......................... 560/55, 179, 183; 562/465, 579; 564/80; 568/339, 591, 820; 549/265

(56) References Cited

PUBLICATIONS

Jai–Wen Chang et al., "Enantioselective Synthesis of α–Hydroxy Acids Employing (IS)–(+)–N, N–Diisopropyl–10–Camphorsulfonamide as Chiral Auxiliary", Organic Letters, vol. 1, No. 13, pp. 2061–2063, (Sep. 1999).

S. Chandrasekhar et al., "Methlenephenylsulfone Appended Acetals and Ketals: New Class of Carbonyl Protective Groups Cleavable by DBU", Tetrahedron Letters, vol. 39, pp. 2401–2404, (Jan. 1998).

*Primary Examiner*—Ba K. Trinh
(74) *Attorney, Agent, or Firm*—Finnegan, Henderson, Farabow, Garrett, & Dunner, L.L.P.

(57) ABSTRACT

The present invention provides a process for preparing optically active α-hydroxy acids and derivatives thereof by subjecting the alkylated 1,3-dioxolanones of formula (IV) wherein $R_1$ and $R_2$ are the same or different and are each independently H or $C_{1-6}$ alkyl; $R_5$ is H, $C_{1-16}$ alkyl, or unsubstituted or substituted phenyl; and $R_6$ is $C_{1-8}$ alkyl, $C_{2-7}$ alkenyl or unsubstituted or substituted benzyl, to either alcoholysis or hydrolysis, in which the alkylated 1,3-dioxolanones are obtained by using 10-camphorsulfonamide as a chiral auxiliary.

(IV)

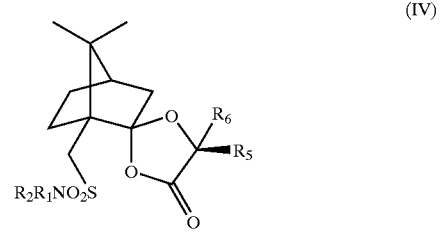

12 Claims, No Drawings

_US 6,639,095 B1_

PROCESS FOR PREPARING OPTICALLY ACTIVE α-HYDROXY ACIDS AND DERIVATIVES THEREOF

This application is a 371 of PCT/US99/28440 filed Dec. 2, 1999.

FIELD OF THE INVENTION

The present invention relates to a process for preparing optically active α-hydroxy acids and derivatives thereof. α-Hydroxy acids are important intermediates for synthesis of organic compounds in pharmaceutical and industrial applications. More particularly, the present invention relates to an enantioselective synthesis for α-hydroxy acids by employing 10-camphorsulfonamide as a chiral auxiliary through 1,3-dioxolanones.

BACKGROUND OF THE INVENTION

Optically active α-hydroxy acids are structural subunits of many natural products, such as motuportin, integerrimine, monocrotaline, and eremantholide A. α-Hydroxy acids and their derivatives are important intermediates for the synthesis of organic compounds in pharmaceutical and industrial applications. A number of useful synthetic methods for the preparation of enantiomertically pure α-branched α-hydroxy acids have been developed. Generally, optically active α-hydroxy acids are obtained through microbial methods, enzymatic syntheses and enantioselective syntheses using chiral auxiliaries.

Microbial methods utilizes microorganism to convert the precursors of α-hydroxy acids, such as oxo- or hydroxy-containing compounds, to produce α-hydroxy acids and derivatives thereof. For example, U.S. Pat. No. 5,326,702 discloses a process for biologically producing an α-hydroxyamide or an α-hydroxy acid, comprising reacting an α-hydroxynitrile or an aldehyde with a microorganism which produces an amide or acid from the corresponding α-hydroxynitrile, in the presence of a sulfite ion, a disulfite ion or a dithionite ion. The related prior art such as U.S. Pat. Nos. 5,371,014, 5,508,181, 5,756,306 and 5,273,895 can also be incorporated herein for reference. However, when using microbial methods, it is difficult to isolate the product from the fermentation broth. The purification for the product is complex and very expensive. Also, the fermentation process usually generates a large amount of waste effluent which harm the environment. An additional treatment process is required and it is not economical.

U.S. Pat. No. 5,098,841 discloses a process for the preparation of the enantiomers of 2-hydroxy-4-phenylbutyric acid, comprising reducing 2-oxo-4-phenyl-butyric acid with the enzyme lactate dehydroaenases in the presence of an electron donor and an enzyme/substrate system. The related prior art utilizing enzymatic syntheses, such as U.S. Pat. Nos. 5,273,895, 5,523,223, 5,686,275 and 5,770,410, can also be incorporated herein for reference. However, purified enzymes are expensive. Therefore, enzymatic syntheses need a stoichiometric amount of expensive cofactors. In addition, the optical purity of an enantioselective product obtained from enzymatic synthesis is highly substrate dependent.

U.S. Pat. Nos. 5,488,131 discloses a method for synthesis of compounds of predetermined chirality that are useful in asymmetric synthesis, comprising the acylation of an enantiomer of pseudoephedrine and then the alkylation of the α-carbon of the adduct, wherein the alkylation proceeds in a stereoselective manner and is directed by the chiral auxiliary pseudoephedrine. The related prior art utilizing enantioselective syntheses using chiral auxiliary, such as U.S. Pat. Nos. 4,983,766, 5,512,682, 5,512,688, 5,516,930, 5,578,730, 5,760,237 and 5,919,949 can also be incorporated therein for reference. There are still some disadvantages when utilizing those enantioselective syntheses. For example, the enantioselectivity of the product is low; chiral auxiliary is very expensive and is not available for large scale production; and the recovery of chiral auxiliary is difficult. Therefore, there remains some room for the development of more efficient methods to produce an optically active compound.

By use of the enantioselectivity of 10-camphorsulfonamide, we have found an enantioselective synthetic method for α-hydroxy acids and derivative thereof through 1,3-dioxolanones by employing 10-camphorsulfonamide as a chiral auxiliary. The process of the present invention does not have the disadvantages encountered in the prior art and has several advantages such as high enantioselectivity of products and high chemical yields. Moreover, both (S) form and (R) form of 10-camphorsulfonamide chiral auxiliaries are commercially available for large scale production and such chiral auxiliaries can be easily recovered in high yield in the process per se. Therefore, the process of the present invention is highly enantioselective, efficient, economic, and easy to do.

SUMMARY OF THE INVENTION

The present invention relates to a process for preparing optically active α-hydroxy acids and derivatives thereof through 1,3-dioxolanones by employing 10-camphorsulfonamide as a chiral auxiliary. The 1,3-dioxolanones are prepared by the catalyzed condensation of a dialkoxy acetal which is derived from the chiral auxiliary, 10-camphorsulfonamide, by treating with α-hydroxy acids. The 1,3-dioxolanones are enantioselective and therefore can be further used to produce optically active compounds such as α-hydroxy acids and derivatives thereof. The 1,3-dioxolanones are subjected to alkylation and then either to alcoholysis or to hydrolysis to produce mono- and disubstituted α-hydroxy acids and derivatives thereof and 10-camphorsulfonamide. 10-camphorsulfonamide can be easily recovered.

DETAILED DESCRIPTION OF THE INVENTION

The present invention relates to an enantioselective synthesis for α-hydroxy acids through 1,3-dioxolanones by employing 10-camphorsulfonamide as a chiral auxiliary.

Generally, the process of the present invention for preparing optically active α-hydroxy acids comprises steps of (a) reacting 10-camphorsulfonamide of formula I

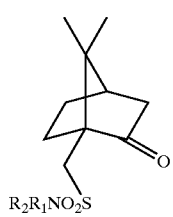

wherein $R_1$ and $R_2$ are the same or different and are each independently H or $C_{1-6}$ alkyl, with alkoxy-substituted alkane to form dialkoxy acetal of formula II

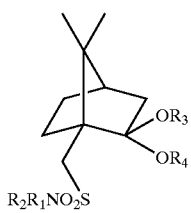

II wherein $R_1$ and $R_2$ are the same or different and are each independently H or $C_{1-6}$ alkyl, $R_3$ and $R_4$ are the same or different and are each independently $C_{1-4}$ alkyl;

(b) reacting the dialkoxy acetal of formula II with an α-hydroxy acid having the formula

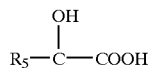

wherein $R_5$ is H, $C_{1-16}$ alkyl, or unsubstituted or substituted phenyl, to form 1,3-dioxolanones of formula III

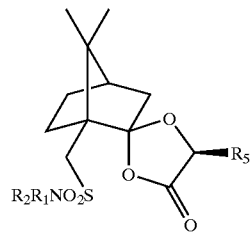

III wherein $R_1$ and $R_2$ are the same or different and are each independently H or $C_{1-6}$ alkyl, and $R_5$ is H, $C_{1-16}$ alkyl, or unsubstituted or substituted phenyl;

(c) reacting the 1,3-dioxolanones of formula III with alkylation reagents to form alkylated 1,3-dioxolanones of formula IV

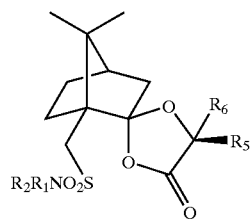

IV wherein $R_1$ and $R_2$ are the same or different and are each independently H or $C_{1-6}$ alkyl, $R_5$ is H, $C_{1-16}$ alkyl, or unsubstituted or substituted phenyl, and $R_6$ is $C_{1-8}$ alkyl, $C_{2-7}$ alkenyl or unsubstituted or substituted benzyl;

(d) subjecting the alkylated 1,3-dioxolanones of formula IV to either
  (i) alcoholysis, when $R_5$ is H, to form 10-camphorsulfonamide and α-hydroxy acids derivatives of formula V

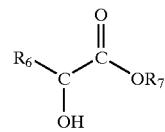

V wherein $R_7$ is $C_{1-6}$ alkyl, and $R_6$ is $C_{1-8}$ alkyl, $C_{2-7}$ alkenyl or unsubstituted or substituted benzyl, or
  (ii) hydrolysis, when $R_5$ is $C_{1-16}$ alkyl or unsubstituted or substituted phenyl, to form 10-camphorsulfonamide and α-hydroxy acids of formula VI

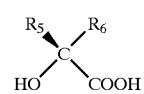

VI wherein $R_5$ is H, $C_{1-16}$ alkyl, or unsubstituted or substituted phenyl, and $R_6$ is $C_{1-8}$ alkyl, $C_{2-7}$ alkenyl or unsubstituted or substituted benzyl.

The starting material, 10-camphorsulfonamide of formula I, for the process of the present invention is generally known and available in the art. In step (a), the 10-camphorsulfonamide of formula I reacts with alkoxy-substituted alkane to form a dialkoxy acetal of formula II. The reaction can be conducted in the absence or presence of catalysts and solvents known to persons skilled in the art. Catalysts such as p-toluene sulfonic acid (p-TSA) and solvents such as alcohols, for example, methanol, are commonly used. In the preferred embodiment of the present invention, the alkoxy-substituted alkane used is $(CH_3O)_3CH$.

In step (b), the dialkoxy acetal of formula II produced from step (a) is subjected to Lewis acid-catalyzed condensation with an α-hydroxy acid having the formula $R_5C(OH)COOH$, wherein $R_5$ is H, $C_{1-16}$ alkyl, or unsubstituted or substituted phenyl, to produce 1,3-dioxolanones of formula III. The reaction conditions for Lewis acid-catalyzed condensation is known in the state of art. Reference can be made to sources such as Farines, M.; Soulier, *J. Bull. Soc. Chim. Fr.* 1970, 332; Petasis, N. A.; Lu, S.-P. *J. Am. Chem. Soc.* 1995, 117,6394; Pearson, W. H.; Cheng, M.-C. *J. Org. Chem.* 1987, 52, 1353; and Hoye, T. R.; Peterson, B. H.; Miller, J. D. *J. Org. Chem.* 1987, 52, 1351. In the embodiment of the present invention, the dialkoxy acetal is reacted with α-hydroxy acid, preferably, glycolic acid, lactic acid and mandelic acid, under an inert gas, at a temperature from about −35° C. to about −60° C., in the presence of ethers as the solvent. The Lewis acid used in the preferred embodiment of the present invention is $BF_3.OEt_2$.

Due to the enantioselectivity of 10-camphorsulfonamide of formula I, the product 1,3-dioxolanones of formula III are also enantioselective. Therefore, the enantioselective 1,3-dioxolanones of formula III is very useful to prepare optically active compounds such as α-hydroxy acids and derivatives thereof.

When $R_5$ is H, the reaction of step (b) may produce a small amount of by-product of 1,3-dioxolanones having formula IIIa

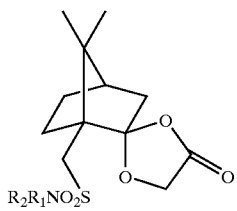

IIIa wherein $R_1$ and $R_2$ are the same of different and are each independently H or $C_{1-6}$ alkyl. The 1,3-dioxolanones of formulae III and IIIa are diastereomeric chiral compounds. Pure 1,3-dioxolanones of formula III can be obtained by recrystallization, or separated from their minor isomers of the 1,3-dioxolanones of formula IIIa by column chromatography. The conditions for recrystallization and column chromatography are well known to persons skilled in the art.

When $R_5$ is $C_{1-16}$ alkyl or unsubstituted or substituted phenyl, the 1,3-dioxolanones of formula III are single products. The stereochemistry of 1,3-dioxolanones can be confirmed by known methods commonly used in the art such as X-ray crystallographic analysis and nuclear overhauser effect (NOE) experiments.

In the alkylation of step (c), 1,3-dioxolanones of formula III are reacted with alkylation reagents such as $R_6X$ wherein $R_6$ is $C_1$–$C_8$ alkyl, $C_2$–$C_7$ alkenyl or unsubstituted or substituted benzyl, and X is a leaving group, to form the alkylated 1,3-dioxolanones of formula IV. Preferably, the alkylation reagent is a halide or sulfonate. The alkylation is conducted under a temperature from –110° C. to room temperature, preferably from –100° C. to 0° C., more preferably from –100° C. to 45° C., most preferably from –100° C. to –78° C., in the presence of a strong base, such as lithium diisopropylamide (LDA), in the absence or presence of solvents. It is found that when deprotonation and the addition of an alkylation reagent were conducted at –100° C. then increased the temperature to –78° C., the diastereoselectivity and the yield of the products can be improved. In the alkylation, no diastereoisomers are detected by 400 MHz $^1$H NMR measurement. The alkylated 1,3-dioxolanones of formulae IV have excellent diastereoselectivity. The stereochemistry of the alkylated 1,3-dioxolanones of formulae IV can be detected by conventional manners such as X-ray crystallographic analysis.

In step (d), the alkylated 1,3-dioxolanones of formula IV can be further subjected to alcoholysis or hydrolysis to produce α-hydroxy acids of formula VI and derivatives thereof of formula V. When $R_5$ is H, the alkylated products is subject to alcoholysis of step (i). In the preferred embodiment of the present invention, the alcoholysis is conducted by heating the alkylated 1,3-dioxolanones of formula IV with anhydrous hydrogen chloride in absolute alcohols with formula $R_7OH$ wherein $R_7$ is $C_{1-6}$ alkyl, such as ethanol. In alcoholysis the 10-camphorsulfonamide of formula I is also produced. The, α-hydroxy acids derivatives of formula VI can be separated and purified by a conventional manner such as column chromatograph). 10-Camphorsulfonamide can therefore be recovered. The reaction scheme of step (d)(i) is shown as follows,

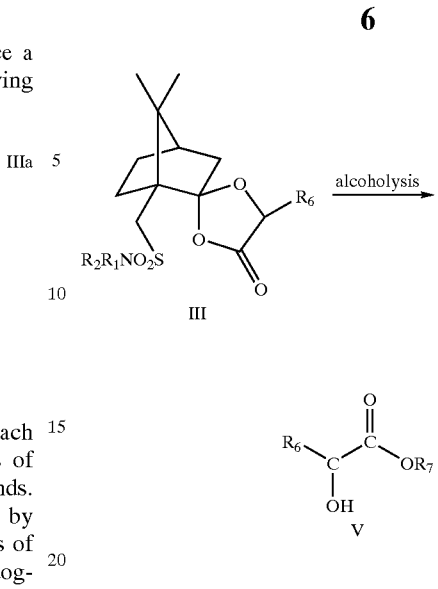

wherein RI and $R_2$ are the same or different and are each independently H or $C_{1-6}$ alkyl, $R_5$ is H, $R_6$ is $C_{1-8}$ alkyl, $C_{2-7}$ alkenyl or unsubstituted or substituted benzyl, and $R_7$ is $C_{1-6}$ alkyl.

When $R_5$ is $C_{1-16}$ alkyl or unsubstituted or substituted phenyl, the alkylated 1,3-dioxolanones of formula IV are subject to the hydrolysis of step (ii). The hydrolysis conditions are conventional in the state of the art. In the preferred embodiment of the present invention, the hydrolysis is conducted by reacting the alkylated 1,3-dioxolanones of formula IV with a strong base such as NaOH in the presence of alcohols, such as methanol, as the solvent. In hydrolysis, the 10-camphorsulfonamide of formula I is also produced, 10-Camphorsulfonamide can be separated by a conventional method such as extraction and recovered. The purification of α-hydroxy acids can be conducted by concentration. The reaction scheme of step (d)(ii) is shown as follows,

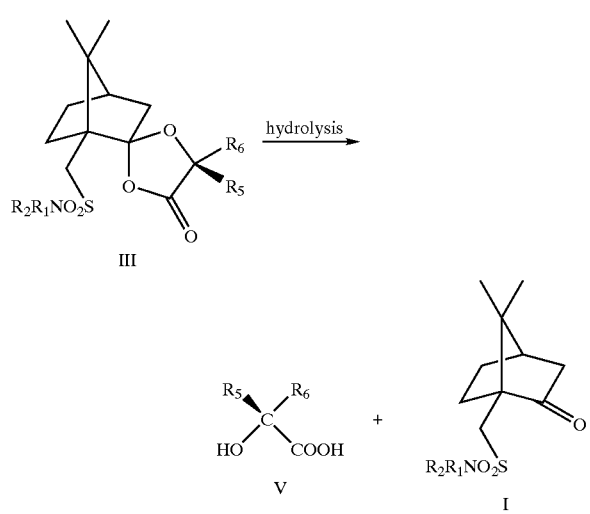

wherein $R_1$ and $R_2$ are the same or different and are each independently H or $C_{1-6}$ alkyl, $R_5$ is $C_{1-16}$ alkyl or unsubstituted or substituted phenyl, and $R_6$ is $C_{1-8}$ alkyl, $C_{2-7}$ alkenyl or unsubstituted or substituted benzyl.

The α-hydroxy acids and derivatives thereof are important intermediates for synthesis of optically active organic compounds in pharmaceutical and industrial applications.

The process of the present invention is further illustrated by the following examples which are provided for illustration but not intended for limitation of the scope of the invention.

Abbreviations: Me means methyl, Et means ethyl, and Ac means COCH$_3$.

WORKING EXAMPLES

Example 1

Example 1 illustrates the preparation of the dialkoxy acetal of formula II from the 10-camphorsulfonamide of formula I.

(1R)-N,N-Diisopropyl-(2,2-dimethoxy-7,7-dimethylbicyclo[2.2.1]hept-1-yl)methanesulfonamide

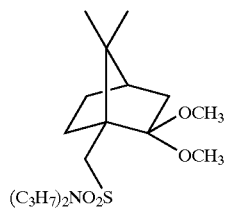

A mixture of 30 g of (1S)-(+)-N,N-diisopropyl-10-camphorsulfonamide, 1 g of p-Toluene sulfonic acid (p-TSA) and 84 mL of CH(OCH$_3$)$_3$ in 150 mL of MeOH was stirred for 84 hours at room temperature. The solution was quenched with 100 mL of saturated NaHCO$_3$(aq), and MeOH was evaporated under reduced pressure. The residue was extracted with ethyl acetate (3×100 mL). The combined organic phases were washed with brine, dried with Na$_2$SO$_4$ (s), evaporated in vacuo, and the residue was purified by column chromatography (SiO$_2$, hexane-EtOAc, 8:1, added 1~2% N(C$_2$H$_5$)$_3$) to give 31.46 g (85%) of (1R)-N,N-diisopropyl-(2,2-dimethoxy-7,7-dimethylbicyclo[2.2.1]hept-1-yl)methanesulfonamide as white solid.

mp=73.8–74.6° C.; [α]D$^{25}$+16.54 (c1.00, CHCl$_3$); IR (KBr) 2973, 2871, 2836, 1748, 1460, 1402, 1377, 1330, 1199, 1136 cm$^{-1}$. $^1$H NMR (CDCl$_3$, 400 MHz) δ 3.70 (hept, J=6.8 Hz, 2H), 3.46 (d, J=15.6 Hz, 1H), 3.30 (s, 3H), 3.13 (s, 3H), 2.72 (d, J=15.6 Hz), 2.29 (td, J=12.6, J=5.2 Hz, 1H), 2.16 (dt, J=13.2, J=3.6 Hz, 1H), 1.91 (ddd, J=7.7, J=7.7, J=3.6 Hz), 1.84–1.76 (m, 1H), 1.63 (t, J=4.8 Hz, 1H), 1.30 (d, J=6.8 Hz, 6H), 1.29 (d, J=6.8 Hz, 6H), 1.28–1.22 (m, 1H), 1.18 (d, J=13.2 Hz, 1H), 0.99 (s, 3H), 0.88 (s, 3H); $^{13}$C NMR (CDCl$_3$, 100.6 MHz) δ 108.5, 53.3, 52.1, 51.1, 49.4, 48.2, 47.4, 43.0, 41.2, 27.0, 24.7, 22.4, 22.2, 21.5, 20.4; Analysis Calculated for C$_{18}$H$_{35}$NO$_4$S: C, 59.80; H, 9.76; N, 3.87; S, 8.87. Found: C, 60.07; H, 9.60; N, 4.22; S, 8.51.

Example 2a–d

Example 2a–d illustrates the preparation of the 1,3-dioxolanones of formula III and IIIa from the dialkoxy acetal of formula II by Lewis acid-catalyzed condensation. General procedures for Lewis acid-catalyzed condensation of the dialkoxy acetal with α-hydroxy acids are as follows:

A solution of the dialkoxy acetal (1 mmol) in CH$_2$Cl$_2$ (1 mL) was added to the mixture of α-hydroxy acid and BF$_3$·O(C$_2$H$_5$)$_2$ (1.6 eq) in (C$_2$H$_5$)$_2$O over 10 min at −50° C. under argon. After stirring about 30 to 60 min, the reaction was quenched with (C$_2$H$_5$)$_3$N (0.6 mL). The solution was poured into 5 mL of iced water and extracted with (C$_2$H$_5$)$_2$O (3×20 mL). The combined organic phases were washed with brine, dried (Na$_2$SO$_4$), evaporated in vacuo and the residue was purified by column chromatography (SiO$_2$, hexane-EtOAc, 6:1) to give the condensation product of 1,3-dioxolanones.

Example 2a (1R,2S)-N,N-Diisopropyl-[2-spiro-2'-(1'-3'-dioxolane-4'-one)-7,7-dimethyl-bicyclo[2.2.1]hept-1-yl]methanesulfonamide

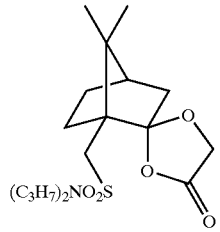

The title compound is prepared from the condensation of (1R)-N,N-diisopropyl-(2,1-dimethoxy-7,7-dimethylbicyclo[2.2.1]hept-1-yl)methane-sulfonamide with glycolic acid (2.2 eq).

74% yield; mp=140.3–140.7° C.; [α]D$^{25}$−7.99 (c1.00, CHCl$_3$); IR (KBr) cm$^{-1}$ 2974, 2879, 1806, 1468, 1394, 1281, 1258, 1338, 1258, 1243, 1198, 1154; $^1$H NMR (CDCl$_3$, 400 MHz) δ 4.44 (d, J=14.2 Hz, 1H), 4.28 (d, J=14.2 Hz, 1H), 3.68 (hept, J=6.8 Hz, 2H), 3.30 (d, J=13.2 Hz, 1H), 2.56 (d, J=13.2 Hz, 1), 2.38–2.26 (m, 2H), 1.80–1.90 (m, 3H), 1.76 (d, J=13.6 Hz, 1H), 1.39–1.38 (m, 1H), 1.28 (d, J=6.8 Hz, 3H), 1.27 (d, J=6.8, 3H), 0.99 (s, 3H), 0.87 (s, 3H); $^{13}$C NMR (CDCl$_3$, 100.6 MHz) δ 171.0, 119.2, 64.7, 54.6, 52.4, 48.3, 45.5, 44.0, 26.1, 26.6, 22.36, 22.2, 20.5, 20.1, Anal. Calcd for C$_{18}$H$_{31}$NO$_5$S: C, 57.88; H, 8.37; N, 3.75; S, 8.59. Found: C, 57.36; H, 8.34; N, 3.65; S, 8.61.

Example 2b (1R,2R)-N,N-Diisopropyl-[2-spiro-2'-(1'-3'-dioxolane-4'-one)-7,7-dimethylbicyclo[2.2.1]hept-1-yl]methanesulfonamide

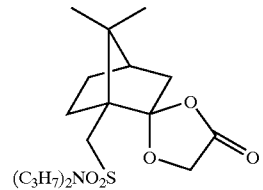

The title compound is a by-product from the process for the preparation of (1R,2S)-N,N-diisopropyl-[2-spiro-2'-(1'-3'-dioxolane-4'-one)-7,7-dimethyl-bicyclo[2.2.1]hept-1-yl]methanesulfonamide.

mp=139.9–140.2° C.; [α]D$^{25}$−13.35 (c 1.00, CHCl$_3$); IR (KBr) 2997, 2968, 2934, 1800, 1458, 1333, 1270, 1240, 1199, 1174, 1136 cm$^{-1}$; $^1$H NMR (CDCl$_3$, 400 MHz) 64.42 (d, J=14.6 Hz, 1H), 4.11 (d, J=14.6 Hz, 1H), 3.69 (hept, J=6.8 Hz, 2H), 3.17 (d, J=14 Hz, 1H), 2.59 (d, J=14 Hz, 1H), 2.50–2.40 (m, 1H), 2.26 (dt, J=13.2, 2.8 Hz, 1H), 1.84–1.72

(m, 3H), 1.69 (d, J=14 Hz, 1H), 1.38–1.30 (m, 1H), 1.27 (d, J=7.2 Hz, 12H); 1.00 (s, 3H); 0.88 (s, 3H); $^{13}$C NMR (CDCl$_3$, 100.6 MHz) δ 172.2, 118.3, 62.9, 54.8, 52.3, 50.8, 48.3, 44.8, 44.2, 26.5, 25.2, 22.3, 22.2, 20.4, 20.1; Anal. Calcd for C$_{18}$H$_{31}$NO$_5$S: C, 57.88; H, 8.37; N, 3.75; S, 8.59. Found: C, 57.76; H, 8.24; N, 3.92; S, 8.24.

Example 2c (1R,2S,5'S)-N,N-Diisopropyl-[2-spiro-2'-(5'-methyl-1',3'-dioxolane-4'-one)-7,7-dimethylbicyclo[2.2.1]hept-1-yl]methanesulfonamide

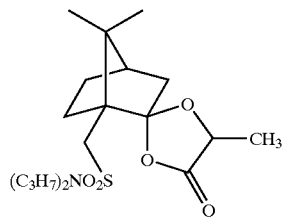

The title compound is prepared from the condensation of (1R)-N,N-diisopropyl-(2,2-dimethoxy-7,7-dimethylbicyclo[2.2.1]hept-1-yl)methanesulfonamide with rac-lactic acid (4.5 eq).

77% yield; mp=94.4–94.6° C.; [α]D$^{25}$+6.36 (c 1.00, CHCl$_3$); IR (neat) 2973, 2949, 2879, 1794, 1370, 1334, 1133, 976, 658 cm$^{-1}$; $^1$H NMR (CDCl$_3$, 400 MHz) δ 4.43 (q, J=6.4 Hz, 1H), 3.70 (hept, J=6.4 Hz, 2H), 3.30 (d, J=13.2 Hz, 1H), 2.56 (d, J=13.2 Hz, 1H), 2.39 (ddd, J=13.2, 9.6, 3.6 Hz, 1H), 2.29 (dt, 1H, J=9.6, 3.6 Hz, 1H), 1.92 (td, J=13.2, 3.6 Hz, 1H), 1.85–1.80 (m, 2H), 1.71 (d, J=13.2 Hz, 1H), 1.53 (d, J=6.4 Hz, 1H), 1.38–1.22 (m, 1H), 1.29 (d, J=6.4 Hz, 6H), 1.1.27 (d, J=6.4 Hz, 6H), 1.02 (s, 3H), 0.90 (s, 3H); $^{13}$C NMR (CDCl$_3$, 100.6 MHz) δ 173.0, 116.2, 70.6. 53.7, 52.1, 50.7, 48.2, 44.2. 43.9. 26.6. 26.1, 22.4, 22.2, 20.5, 20.2, 15.4; MS (EI) m/z (relative intensity) 387 (M$^+$, 0.1), 372 (3), 223 (21), 215 (7), 151 (100), 123 (47), 109 (56), 93 (35); HRMS calcd for C$_{19}$H$_{33}$O$_5$NS(M$^+$-Me) m/z 372.1842, found 372.1847; Anal. Calcd for C$_{19}$H$_{33}$O$_5$NS: C, 58.89; H, 8.58; N, 3.61; S, 8.27; Found: C, 58.79; H, 8.34; N, 3.64; S, 8.30.

Example 2d (1R,2S,5'S)-N,N-Diisopropyl-[2-spiro-2'-(5'-phenyl-1',3'-dioxolane-4'-one)-7,7-dimethylbicyclo[2.2.1]hept-1-yl]methanesulfonamide

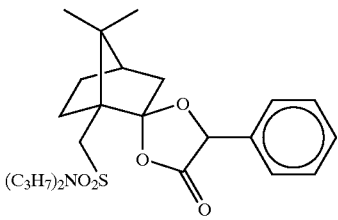

The title compound is prepared from the condensation of (1R)-N,N-diisopropyl-(2,2-dimethoxy-7,7-dimethylbicyclo[2.2.1]hept-1-yl)methanesulfonamide with rac-mandelic acid (2.2 eq).

56% yield; Chromatography on silica gel (hexane-EtOAc, 6:1); mp=112.3–112.6° C.; [α]D$^{25}$+2.29 (c1.00, CHCl$_3$); IR (KBr) 3070, 2970, 2879, 1799, 1458, 1335, 1121, 977, 774 cm$^{-1}$; $^1$H NMR (CDCl$_3$, 400 MHz) δ 7.61–7.59 (m, 2H), 7.36–7.32 (m, 3H), 5.36 (s, 1H), 3.43 (hept, J=6.9 Hz, 1H), 3.28 (d, J=13.7 Hz, 1H), 2.53 (d, J=13.7 Hz, 1H), 2.46 (dt, J=13.4, 4.0 Hz, 1H), 2.34–2.29 (m, 1H), 2.09 (dt, J=5.1, 13.4 Hz, 1H), 1.90–1.80 (m, 4H), 1.41–1.35 (m, 1H), 1.16 (d, J=6.9 Hz, 6H), 1.22 (d, J=6.9 Hz, 6H), 1.07 (s, 3H), 0.94 (s, 3H); $^{13}$C NMR (CDCl$_3$, 100.6 MHz) δ 170.2, 133.4, 128.6, 128.3, 127.3, 116.6, 75.0, 53.9, 51.7, 50.6, 48.0, 44.2, 44.0, 26.6, 25.7, 22.7, 21.6, 20.6, 20.2; MS (EI) m/z (relative intensity) 449 (M$^+$, 0.04), 434 (4), 284 (7), 257 (10), 151 (100), 123 (42), 109 (60), 93 (21), 81 (38), 67 (21); HRMS calcd for C$_{24}$H$_{35}$O$_5$NS (M$^+$-Me) m/z 434.1999, found 434.2003; Anal. Calcd for C$_{24}$H$_{35}$O$_5$NS: C, 64.11; H, 7.85; N, 3.12; S, 7.13; Found: C, 64.00; H, 7.64; N, 3.27; S, 7.16.

Example 3a–i

Example 3a–i illustrate the alkylation of 1,3-dioxolanones of formula III wherein R$_5$ is H.

Example 3a (1R,2S,5'R)-N,N-Diisopropyl-[2-spiro-2'-(5'-methyl-1'-3'-dioxolane-4'-one)-7,7-dimethylbicyclo[2.2.1]hept-1-yl]methanesulfonamide

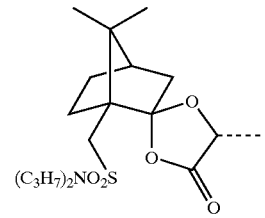

A solution of lithium diisopropylamide (LDA) in tetrahydrofuran (THF) (1.0 mL) was prepared under argon from diisopropylamine (0.14 mL, 1.0 mmol) and n-Butyl-Li solution (2.2 M solution in hexane, 0.44 mL) at 0° C. After stirring for 30 min, hexamethyl phosphorarnide (HMPA) (1.2eq) was added and cooling to −78° C. A solution of (1R,2S)-N,N-diisopropyl-[2-spiro-2'-1'-3'-dioxolane-4'-one)-7,7-dimethyl-bicyclo[2.2.1]hept-1-yl] methanesulfonamide (0.8 mmol) in THF (1.0 mL) was added over 20 min, and the mixture was allowed to stir for 30 min, then the methyl halide (1.5 eq) was added. The mixture was stirred for 1 hour. To the mixture was added 1% H$_2$C$_2$O$_4$(aq) (1 mL) and warmed to 0° C. and neutralized with 1% H$_2$C$_2$O$_4$(aq) to pH=6~7. The solution was extracted with EtOAc, the combined organic phases were washed with brine, dried (Na$_2$SO$_4$), evaporated in vacuo and the residue was purified by column chromatography on silica gel to give the title compound. The diastereoselectivity of the product is 93.5%.

77% Yield; Chromatography on silica gel (hexane-EtOAc, 6:1); mp=106.0–107.0° C.; [α]D$^{25}$−17.67 (c 1.00, CHCl$_3$); IR (KBr) 3002, 2973, 2886, 1801, 1457, 14134, 1375, 1328, 1283, 1257, 1240, 1200, 1154, 1117, 1034 cm$^{-1}$; $^1$H NMR (CDCl$_3$, 400 MHz) δ 4.60 (quat, J=6.8 Hz, 1H), 3.68 (hept, J=6.8 Hz, 2H), 3.28 (d, J=13.6 Hz, 1H), 2.55 (d, J=13.6 Hz, 1H), 2.37–2.24 (m, 2H), 1.90–1.76 (m, 4H), 1.43 (d, J=7.2 Hz 3H), 1.40–1.30 (m, 1H), 1.271 (d, J=6.8, Hz, 6H), 1.268 (d, J=6.8, 6H), 1.00 (s, 3H), 0.87 (s, 3H); $^{13}$C NMR (CDCl$_3$, 100.6 MHz) δ 173.7, 117.5, 72.3, 54.8, 52.5, 51.2, 48.3, 47.2, 44.1, 26.6, 25.9, 22.5, 22.2, 20.6, 20.2, 19.0; Anal. Calcd for C$_{19}$H$_{33}$O$_5$NS: C, 58.89; H, 8.58; N, 3.61; S, 8.27; Found: C, 58.87; H, 8.50; N, 3.91; S, 8.65.

Example 3b

Example 3a was repeated except that HMPA was not added and the reaction is conducted at temperature of −100° C. increased to −78° C. The title compound was produced with 84% yield and >98% of diastereoselectivity.

Example 3c

Example 3a was repeated except that the reaction is conducted at temperature of −100° C. increased to −78° C. The title compound was produced with 86% yield and >98% of diastereoselectivity.

Example 3d (1R,2S,5'S)-N,N-Diisopropyl-{2-spiro-2'-[5'-(prop-2"-enyl)-1'-3'-dioxolane-4'-one]-7,7-dimethylbicyclo[2.2.1]hept-1-yl}methanesulfonamide

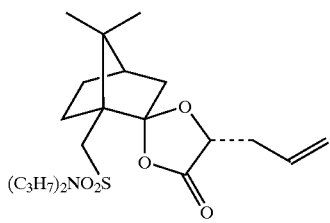

A solution of lithium diisopropylamide (LDA) in tetahydrofuran (THF) (1.0 mL) was prepared under argon from diisopropylamine (0.14 mL, 1.0 mmol) and n-Butyl-Li solution (2.2 M solution in hexane, 0.44 mL) at 0° C. After stirring for 30 min, the reaction is cooled to −100° C. A solution of (1R,2S)-N,N-diisopropyl-[2-spiro-2'-(1'-3'-dioxolane-4'-one)-7,7-dimethyl-bicyclo[2.2.1]hept-1-yl]methanesulfonamide (0.8 mmol) in THF (1.0 mL) was added over 20 min, and the mixture was allowed to stir for 30 min, then the allyl halide (1.5 eq) was added. The mixture was allowed to warm to −78° C., and stirred for 1 hour. To the mixture was added 1% $H_2C_2O_4$(aq) (1 mL) and warmed to 0° C. and neutralized with 1% $H_2C_2O_4$(aq) to pH=6~7. The solution was extracted with EtOAc, the combined organic phases were washed with brine, dried ($Na_2SO_4$), evaporated in vacuo and the residue was purified by column chromatography on silica gel to give the desired compound. The diastereoselectivity of the product is >98%.

76% Yield; Chromatography on silica gel (hexane-EtOAc, 6:1); mp=149.5–151.4° C.; $[\alpha]D^{25}$−3.77 (c 1.00, $CHCl_3$); IR (KBr) 3007, 2973, 2881, 1798, 1332, 1283, 1240, 1201, 1153, 1136 cm$^{-1}$. $^1$H NMR ($CDCl_3$, 400 MHz) δ 5.74–5.85 (m, 1H), 5.20–5.13(m, 2H), 4.62 (dd, J=6.8, J=4.8 Hz, 1H), 3.68 (hept, J=6.8 Hz, 2H), 3.29 (d, J=13.6 Hz, 1H), 2.64–2.50 (m, 1H), 2.56 (d, J=13.6 Hz, 1H), 2.62–2.54 (m, 1H), 2.48–2.23 (m, 2H), 1.90–1.73 (m, 4H), 1.38–1.30 (m, 1H, 1.28 (d, J=6.8 Hz, 6H), 1.27 (d, J=6.8 Hz, 6H), 0.99 (s, 3H), 0.86 (s, 3H); $^{13}$C NMR ($CDCl_3$, 100.6 MHz) δ 172.3, 132.1, 118.9, 117.6, 75.8, 54.7, 52.3, 51.0, 48.2, 47.2, 43.8, 36.7, 26.4, 25.7, 22.4, 22.0, 20.4, 20.0; Anal. Calcd for $C_{21}H_{35}O_5NS$: C, 60.99; H, 8.53; N, 3.39; S, 7.75; Found: C, 60.65; H, 8.85; N, 3.27; S, 7.90.

Example 3e

Example 3d was repeated except that HMPA was added. The title compound is produced with 76% yield and >98% of diastereoselectivity.

Example 3f (1R,2S,5'R)-N,N-Diisopropyl-[2-spiro-2'-(5'-ethyl-1',-3'-dioxolane-4'-one)-7,7-dimethylbicyclo[2.2.1]hept-1-yl]methanesulfonamide

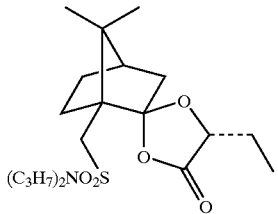

A solution of lithium diisopropylamide (LDA) in tetahydrofuran (THF) (1.0 mL) was prepared under argon from diisopropylamine (0.14 mL, 1.0 mmol) and n-Butyl-Li solution (2.2 M solution in hexane, 0.44 mL) at 0° C. After stirring for 30 min, hexamethyl phosphoramide (HMPA) (1.2 eq) was added and cooling to −78° C. A solution of (1R,2S)-N,N-diisopropyl-[2-spiro-2'-(1'-3'-dioxolane-4'-one)-7,7-dimethyl-bicyclo[2.2.1]hept-1-yl]methanesulfonamide (0.8 mmol) in THF (1.0 mL) was added over 20 min, and the mixture was allowed to stir for 30 min, then the ethyl halide (1.5 eq) was added. The mixture was stirred for 1 hour. To the mixture was added 1% $H_2C_2O_4$(aq) (1 mL) and warmed to 0° C. and neutralized with 1% $H_2C_2O_4$(aq) to pH=6~7. The solution was extracted with EtOAc, the combined organic phases were washed with brine, dried ($Na_2SO_4$), evaporated in vacuo and the residue was purified by column chromatography on silica gel to give the desired compound. The diastereoselectivity of the product is >98%. 57% Yield of (1S)-(+)-N,N-diisopropyl-10-camphorsulfonamide was recovered.

36% Yield; Chromatography on silica gel (hexane-EtOAc, 6:1); mp=143.1–143.8° C.; $[\alpha]D^{25}$−7.17 (c 1.00, $CHCl_3$); IR (KBr) 3002, 2968, 2949, 2891, 1800, 1328, 1238, 1155, 1136 cm$^{-1}$; $^1$H NMR ($CDCl_3$, 400 MHz) δ 4.49 (dd, J=6,6, J=4.8 Hz, 1H), 3.69 (hept, J=6.8 Hz, 2H), 3.30 (d, J=13.6, 1H), 2.57 (d, J=13.6 Hz, 1H), 2.36–2.24 (m, 2H), 1.93–1.68 (m, 6H), 1.39–1.31 (m, 1H), 1.284 (d, J=6.8 Hz, 6H), 1.278 (d, J=13.6 Hz, 6H), 1.006 (s, 3H), 1.004 (t, J=7.2 Hz, 3H), 0.87 (s, 3H); $^{13}$C NMR ($CDCl_3$, 100.6 MHz) δ 173.0, 117.5, 77.2, 54.8, 52.4, 51.1, 48.3, 47.0, 43.9, 26.5, 25.72, 25.68, 22.5, 22.1, 20.5, 20.1, 9.3; Anal. Calcd for $C_{20}H_{35}O_5NS$: C, 59.82; H, 8.79; N, 3.49, S, 7.99; Found: C, 59.82; H, 8.77; N, 3.77; S, 7.96.

Example 3g

Example 3f was repeated except that the reaction was conducted at the temperature of −100° C. increased to −78° C. The title compound is produced with 65% yield and >98% of diastereoselectivity.

Example 3h (1R,2S,5′R)-N,N-Diisopropyl-[2-spiro-2′-(5′-phenylmethyl-1′,-3′-dioxolane-4′-one)-7,7-dimethylbicyclo[2.2.1]hept-1-yl] methanesulfonamide

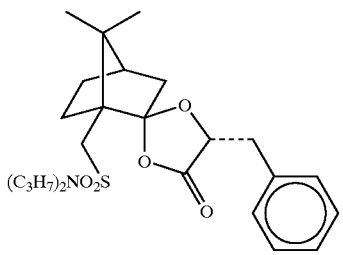

A solution of lithium diisopropylamide (LDA) in tetrahydrofuran (THF) (1.0 mL) was prepared under argon from diisopropylamine (0.14 mL, 1.0 mmol) and n-Butyl-Li solution (2.2 M solution in hexane, 0.44 mL) at 0° C. After stirring for 30 min, hexamethyl phosphoramide (HMPA) (1.2 eq) was added and cooling to −78° C. A solution of (1R,2S)-N,N-diisopropyl-[2-spiro-2′-(1′-3′-dioxolane-4′-one)-7,7-dimethyl-bicyclo[2.2.1]hept-1-yl] methanesulfonamide (0.8 mmol) in THF (1.0 mL) was added over 20 min, and the mixture was allowed to stir for 30 min, then the benzyl halide (1.5 eq) was added. The mixture was allowed to warm to −45° C., and stirred for 1 hour. To the mixture was added 1% $H_2C_2O_4$(aq) (1 mL) and warmed to 0° C. and neutralized with 1% $H_2C_2O_4$(aq) to pH=6~7. The solution was extracted with EtOAc, the combined organic phases were washed with brine, dried ($Na_2SO_4$), evaporated in vacuo and the residue was purified by column chromatography on silica gel to give the desired compound. The diastereoselectivity of the product is >98%.

60% Yield; Chromatography on silica gel (hexane-EtOAc, 6:1); mp=106.3–161.0° C.; $[\alpha]D^{25}$+1.78 (c 1.00, $CHCl_3$); IR (KBr) 2992, 2944, 2886, 1787, 1336, 1240, 1199, 1149, 1134 $cm^{-1}$; $^1H$ NMR ($CDCl_3$, 400 MHz) δ 7.30–7.20 (m, 5H), 4.83 (t, J=5.2 Hz, 1H), 3.67 (hept, J=6.8 Hz, 2H), 3.25 (d, J=13.2 Hz, 1H), 3.25 (d, J=13.2 Hz, 1H), 3.08 (d, J=5.2 Hz, 2H), 2.51 (d, J=13.2 Hz, 1H), 2.42 (m, 1H, 1.82 (td, J=12.6, 1H), 1.76–1.60 (m, 3H), 1.26 (d, J=6.8 Hz, 12H), 1.30–1.18 (m, 1H), 1.16 (d, J=13.6 Hz 1H), 0.91 (s, 3H), 0.8 (s, 3H); $^{13}C$ NMR ($CDCl_3$, 100.6 MHz) δ 172.5, 136.2, 129.8, 128.3, 126.9, 118.0, 77.4, 54.8, 52.4, 51.0, 48.3, 45.9, 43.7, 38.1, 26.4, 25.7, 22.5, 22.0, 20.4, 20.1; Anal. Calcd for $C_{25}H_{37}O_5NS$: C, 64.76; H, 8.04; N, 3.02; S, 6.92; Found: C, 64.76; H, 8.00; N, 3.43; S, 7.11.

Example 3i

Example 3h was repeated except that the reaction is conducted at the temperature of −100° C. increased to −78° C. The title compound is produced with 70% yield and >98% of diastereoselectivity.

Example 4a–v

Example 4a–g illustrates the alkylation of 1,3-dioxolanones of formula III wherein $R_5$ is methyl or phenyl. The general procedures for the alkylation are as follows:

A solution of lithium diisopropylamide (LDA) in tetrahydrofuran (THF) (1.0 mL) was prepared under argon from diisopropylamine (0.14 mL, 1.0 mmol) and n-Butyl-Li solution (2.2 M solution in hexane, 0.44 mL) at 0° C. After stirring for 30 min, the reaction is cooled to −100° C. A solution of 1,3-dioxolanone of formula III (0.8 mmol) in THF (1.0 mL) was added over 20 min, and the mixture was allowed to stir for 30 min, then the alkylation reagent (1.5 eq) was added. The mixture was allowed to warm to −78° C., and stirred for 1 hour. To the mixture was added 1% $H_2C_2O_4$(aq) (1 mL) and warmed to 0° C. and neutralized with 1% $H_2C_2O_4$(aq) to pH=6~7. The solution was extracted with EtOAc, the combined organic phases were washed with brine, dried ($Na_2SO_4$), evaporated in vacuo and the residue was purified by column chromatography on silica gel (hexane-ether, 4:1) to give the desired compound.

Example 4a (1R,2S,5′R)-N,N-Diisopropyl-[2-spiro-2′-(5′-ethyl-5′-methyl-1′,-3′-dioxolane-4′-one)-7,7-dimethylbicyclo[2.2.1]hept-1-yl] methanesulfonamide

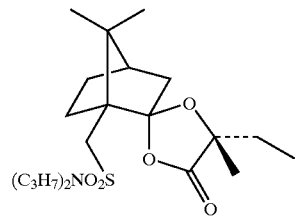

The title compound was prepared by reacting (1R,2S,5′S)-N,N-diisopropyl-[2-spiro-2′-(5′-methyl-1′,3′-dioxolane-4′-one)-7,7-dimethyl-bicyclo[2.2.1]hept-1-yl] methanesulfonamide with ethyl halide according to the general procedures. The diastereoselectivity of the product is >98%.

79% Yield; mp=185.4–185.5° C.; $[\alpha]D^{25}$+9.52 (c 1.00, $CHCl_3$); IR (KBr) 3007, 2977, 1796, 1635, 1458, 1330, 1189, 1148, 1135, 1115, 983, 774 $cm^{-1}$; $^1H$ NMR ($CDCl_3$, 400 MHz) δ 3.69 (hept, J=6.4 Hz, 2H), 3.28 (d, J=13.2 Hz, 1H), 2.58 (d, J=13.2 Hz, 1H), 2.35–2.24 (m, 2H), 2.06–1.98 (m, 1H), 1.84–1.68 (m, 5H), 1.48 (s, 3H), 1.38–1.21 (m, 1H), 1.33 (d, J=6.4 Hz, 6H), 1.28 (d, J=6.4 Hz, 6H), 1.02 (s, 3H), 1.0 (t, J=8.0 Hz, 3H), 0.91 (s, 3H); $^{13}C$ NMR ($CDCl_3$, 100.6 MHz) δ 174.74, 115.1, 80.7, 54.1, 51.8, 50.4, 48.0, 46.5, 44.10, 30.36, 26.36, 25.6, 22.5, 21.7, 20.4, 20.0, 19.7, 7.2; MS (EI) m/z (relative intensity) 415 ($M^+$, 67), 267 (22), 251 (20), 171 (29), 151 (100), 109 (63), 86 (61), 55 (77); HRMS calcd for $C_{21}H_{37}O_5NS$ ($M^+$–Me) m/z 400.2163, found 400.2154; Anal. Calcd for $C_{21}H_{37}O_5NS$: C, 60.69; H, 8.90; N, 3.37; S, 7.72; Found: C, 60.59; H, 8.71; N, 3.43; S, 7.78.

Example 4b (1R,2S,5'R)-N,N-Diisopropyl-[2-spiro-2'-(5'-methyl-5'-propyl-1',3'-dioxolane-4'-one)-7,7-dimethylbicyclo[2.2.1]hept-1-yl)methanesulfonamide

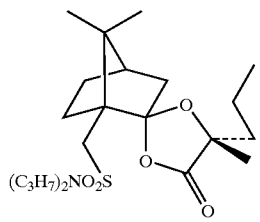

The title compound was prepared by reacting (1R,2S,5'S)-N,-diisopropyl-[2-spiro-2'-(5'-methyl-1',3'-dioxolane-4'-one)-7,7-dimethyl-bicyclo[2.2.1]hept-1-yl] methanesulfonamide with propyl halide according to the general procedures. The diastereoselectivity of the product is >98%.

67% Yield; mp=191.6–191.8° C.; $[\alpha]_D^{25}$+2.17 (c 1.00, CHCl$_3$); IR (KBr) 2965, 2877, 1798, 1635, 1334, 1187, 1114, 1039, 982, 775, 660 cm$^{-1}$; $^1$H NMR (CDCl$_3$, 400 MHz) δ 3.69 (hept, J=6.4 Hz, 2H), 3.27 (d, J=13.6 Hz, 1H), 2.58 (d, J=13.6 Hz, 1H), 2.34–2.23 (m, 2H), 2.06–1.99 (m, 1H), 1.84–1.76 (m, 3H), 1.71–1.21 (m, 5H), 1.49 (s, 3 H), 1.29 (d, J=6.4 Hz, 6H), 1.27 (d, J=6.4 Hz, 6H), 1.01 (s, 3H), 0.93 (t, J=7.2 Hz, 3H), 0.91 (s, 3H); $^{13}$C NMR (CDCl$_3$, 100.6 MHz) δ 174.9, 115.3, 80.6, 54.3, 51.9, 50.4, 48.1, 46.5, 44.3, 39.8, 26.4, 25.7, 22.6, 21.8, 20.5, 20.5, 20.1, 16.4, 14.1; MS (EI) m/z (relative intensity) 429 (M$^+$, 0.2), 151 (32), 123 (15), 109 (25), 86 (75), 84 (100), 69 (9); HRMS calcd for C$_{22}$H$_{39}$O$_5$NS (M$^+$–Me) m/z 414.2349, found 414.2290; Anal. Calcd for C$_{22}$H$_{39}$O$_5$NS: C, 61.51; H, 9.15; N, 3.26; S, 7.46; Found: C, 61.60; H, 9.37; N, 3.34 S, 7.61.

Example 4c (1R,2S,5'R)-N,N-Diisopropyl-{2-spiro-2'-[5'-methyl-5'-(prop-2"-enyl)-1',3'-dioxolane-4'-one]-7,7-dimethylbicyclo[2.2.1]hept-1-yl}methanesulfonamide

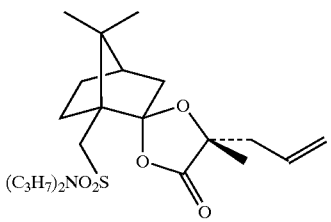

The title compound was prepared by reacting (1R,2S,5'S)-N,N-diisopropyl-[2-spiro-2'-(5'-methyl-1',3'-dioxolane-4'-one)-7,7-dimethyl-bicyclo[2.2.1]hept-1-yl] methanesulfonamide with allyl halide according to the Peneral procedures. The diastereoselectivity of the produrt is >98%.

78% Yield; mp=177.7–177.8° C.; $[\alpha]_D^{25}$+18.65 (c 1.00, CHCl$_3$); IR (KBr) 3007, 2971, 1798, 1645, 1332, 1247, 1185, 1146, 984, 919, 774, 660 cm$^{-1}$; $^1$H NMR (CDCl$_3$, 400 MHz) δ 5.87–5.76 (m, 1H), 5.21–5.14 (m, 2H), 3.69 (hept, J=6.8 Hz, 2H), 3.27 (d, J=14.0 Hz, 1H), 2.57 (d, J=14.0 Hz, 1H), 2.51–2.29 (m, 4H), 1.98 (m, 1H), 1.85–1.77 (m, 3H), 1.55 (s, 3H), 1.38–1.23 (m, 1H), 1.28 (d, J=6.8 Hz, 6H), 1.27 (d, J=6.8 Hz, 6H), 1.01 (s, 3H), 0.91 (s, 3H); $^{13}$C NMR (CDCl$_3$, 100.6 MHz) δ 174.3, 131.1, 119.7, 115.5, 80.1, 54.3, 51.9, 50.5, 48.1, 46.6, 44.2, 41.9, 26.4, 25.7, 22.6, 21.8, 20.6, 20.5, 20.1; MS (EI) m/z (relative intensity) 427 (M$^+$, 0.13), 316 (3), 300 (2), 263 (16), 215 (16), 151 (100), 123 (40), 109 (67), 81 (36), 67 (25); HRMS calcd for C$_{22}$H$_{37}$O$_5$NS (M$^+$–Me) m/z 412.2174, found 412.2147; Anal. Calcd for C$_{22}$H$_{37}$O$_5$NS: C, 61.80; H, 8.72; N, 3.28; S, 7.50; Found: C, 61.57; H, 8.52; N, 3.6; S, 7.51.

Example 4d (1R,2S,5'R)-N,N-Diisopropyl-[2-spiro-2'-(5'-methyl-5'-butyl-1+,3'-dioxolane-4'-one)-7,7-dimethylbicyclo[2.2.1]hept-1-yl]methanesulfonamide

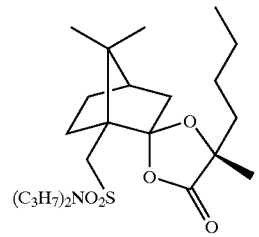

The title compound was prepared by reacting (1R,2S,5'S)-N,N-diisopropyl-[2-spiro-2'-(5'-methyl-1',3'-dioxolane-4'-one)-7,7-dimethyl-bicyclo[2.2.1]hept-1-yl] methanesulfonamide with butyl halide according to the general procedures. The diastereoselectivity of the product is >98%.

74% Yield; mp=148.3–148.5° C.; $[\alpha]_D^{25}$+5.13 (c 1.0, CHCl$_3$); IR (KBr) 2963, 2939, 2876, 1794, 1338, 1148, 1137, 978, 778, 661 cm$^{-1}$; $^1$H NMR (CDCl$_3$, 400 MHz) δ 3.69 (hept, J=6.4 Hz, 2H), 3), 3.27 (d, J=13.6 Hz, 1H), 2.58 (d, J=13.6 Hz, 1H), 2.35–2.23 (m, 2H), 2.06–1.99 (m, 1H), 1.82–1.75 (m, 3H), 1.71–1.64 (m, 2H), 1.49 (s, 3H), 1.39–1.27 (m, 3H), 1.29 (d, J=6.4 Hz, 6H), 1.27 (d, J=6.4 Hz, 6H), 1.02 (s, 3H), 0.92–0.88 (m, 5H), 0.91 (s, 3H); $^{13}$C NMR (CDCl$_3$, 100.6 MHz) δ 175.0, 115.3, 80.6, 54.3, 52.0, 50.6, 48.2, 46.6, 44.3, 37.3, 26.5, 25.8, 25.1, 22.7, 22.6, 22.0, 20.6, 20.5, 20.2, 13.6; MS (EI) m/z (relative intensity) 443 (M$^+$, 0.3), 279 (12), 215 (14), 151 (100), 123 (42), 86 (46), 81 (35), 67 (20); HRMS calcd for C$_{23}$H$_{41}$O$_5$NS (m$^-$–Me) m/z 428.2464, found 428.2476; Anal. Calcd for C$_{23}$H$_{41}$O$_5$NS: C, 62.27; H, 9.32; N, 3.16; S, 7.23; Found: C, 62.15; H, 9.37; N, 3.34; S, 7.33.

Example 4e (1R,2S,5'R)-N,N-Diisopropyl-[2-spiro-2'-(5'-methyl-5'-phenylmethyl-1',3'-dioxolane-4'-one)-7,7-dimethylbicyclo[2.2.1]hept-1-yl]methanesulfonamide

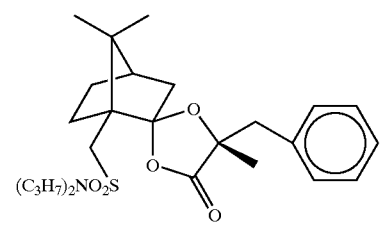

The title compound was prepared by reacting (1R,2S,5'S)-N,N-diisopropyl-[2-spiro-2'-(5'-methyl-1',3'-dioxolane-4'- one)-7,7-dimethyl-bicyclo[2.2.1]hept-1-yl]
methanesulfonamide with benzyl halide according to the
general procedures. The diastereoselectivity of the product
is >98%.

82% Yield; mp=130.4–130.6° C.; $[\alpha]_D^{25}$+32.33 (c 1.0, CHCl$_3$); IR (KBr) 3061, 3027, 2997, 2973, 2944, 2881, 1790, 1333, 1179, 1146, 1119, 797 cm$^{-1}$; $^1$H NMR (CDCl$_3$, 400 MHz) δ 7.32–7.22 (m, 5H), 3.66 (hept, J=6.8 Hz, 2H), 3.22 (d, J=14.0 Hz, 1H), 3.14 (d, J=14.8 Hz, 1H), 2.88 (d, J=14.8 Hz, 1H), 2.60 (d, J=14.0 Hz, 1H), 2.28–2.20 (m, 2H), 2.13–2.06 (m, 1H), 1.83–1.76 (m, 2H), 1.56 (d, J=13.2 Hz, 1H), 1.44 (s, 3H), 1.41–1.42 (m, 1H), 1.26 (d, J=6.8 Hz, 6H), 1.25 (d, J=6.8 Hz, 6H), 1.02 (s, 3H), 0.92 (s, 3H); $^{13}$C NMR (CDCl$_3$, 100.6 MHz) δ 174.6, 135.3, 130.4, 1283, 127.1, 116.5, 81.4, 54.6, 51.9, 50.6, 48.2, 46.1, 44.4, 43.8, 26.4, 25.7, 22.9, 21.9, 21.6, 20.8, 20.2; MS (ED m/z (relative intensity) 447 (M$^+$, 1.4), 313 (100), 300 (17), 215 (56), 151 (61), 123 (12), 109 (10); HRMS cacld for C$_{26}$H$_{39}$O$_5$NS (M$^+$–Me) m/z 477.2584, found 477.2517; Anal. Cacld for C$_{26}$H$_{39}$O$_5$NS: C, 65.38; H, 6.71; N, 2.93; S, 6.71; Found: C, 65.42; H, 6.85; N, 3.03; S, 6.73.

Example 4f (1R,2S,5'S)-N,N-Diisopropyl-[2-spiro-2'-(5'-methyl-
5'-phenyl-1',3'-dioxolane-4'-one)-7,7-
dimethylbicyclo[2.2.1]hept-1-yl]
methanesulfonamide

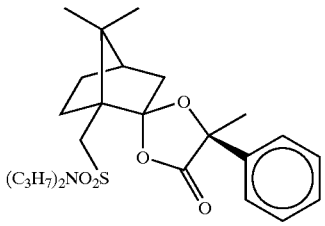

The title compound was prepared by reacting (1R,2S, 5'S)-)-N,N-diisopropyl-[2-spiro-2'-(5'-phenyl-1',3'-dioxolane-4'-one)-7,7-dimethyl-bicyclo[2.2.1]hept-1-yl] methanesulfonamide with methyl halide according to the general procedure. The diastereoselectivity of the product is >98%.

76% Yield; mp=142.2–142.4° C.; $[\alpha]_D^{25}$–18.55 (c 1.0, CHCl$_3$); IR (KBr) 3060, 2982, 2880, 1791, 1639, 1394 cm$^{-1}$; $^1$H NMR (CDCl$_3$, 400 MHz) δ 7.69–7.71 (m, 2H), 7.35–7.23 (m, 3H), 3.09 (d, J=14 Hz, 1H), 2.95 (b, 2H), 2.50–2.45 (m, 1H), 2.45 (d, J=14 Hz, 1H), 2.30–2.23 (m, 1H), 2.11–2.04 (m, 1H), 1.94–1.78 (m, 3H), 1.70 (m, 3H), 1.42–1.36 (m, 1H), 1.15 (s, 3H), 1.02 (d, J=6.4 Hz, 6H), 0.94 (d, J=6.4 Hz, 6H, 0.93 (s, 3H); $^{13}$C NMR (CDCl$_3$, 100.6 MHz) δ 172.7, 140.6, 128.0, 17.1, 124.1. 115.9, 79.8, 54.2. 51.2, 50.4, 47.5, 46.6, 44.2, 30.5, 26.5, 25.3, 22.8, 21.0. 20.5, 20.0; MS (EI) m/z (relative intensity) 464 (M$^+$+1, 1.08), 448 (11) 316 (27), 299 (46), 271 (28), 151 (100), 70 (50); HRMS calcd for C$_{25}$H$_{37}$NO$_5$S (M$^+$) m/z 463.2392, found 463.2400; Anal. Cacld for C$_{25}$H$_{37}$NO$_5$S: C, 64.76; H, 8.04; N, 3.02; S, 6.92; Found: C, 64.76; H, 8.07; N, 3.03; S, 6.92.

Example 4e (1R,2S,5'S)-N,N-Diisopropyl-{2-spiro-2'-(5'-phenyl-
5'-(prop-2''-enyl)-1',3'-dioxolane-4'-one)-7,7-
dimethyl-bicyclo[2.2.1]hept-1-yl}methane
Sulfonamide

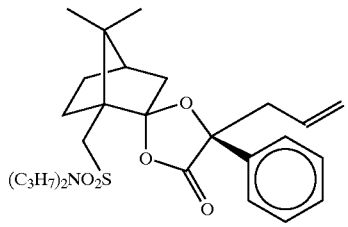

The title compound was prepared by reacting (1R,2S,5'S)-N,N-diisopropyl-[2-spiro-2'-(5'-phenyl-1',3'-dioxolane-4'-one)-7,7-dimethyl-bicyclo[2.2.1]hept-1-yl] methanesulfonamide with allyl halide according to the general procedure. The diastereoselectivity of the product is >98%.

84% Yield; mp=147.5–147.7° C.; $[\alpha]_D^{25}$–19.64 (c 1.0, CHCl$_3$); IR (KBr) 2958, 2880, 1793, 1640, 1615, 1338, 1120, 977, 936, 702, 664 cm$^{-1}$; $^1$H NMR (CDCl$_3$, 400 MHz) δ 7.69–7.67 (m, 2H), 7.35–7.22 (m, 3H), 5.63–5.53 (m, 1H), 5.08–4.97 (m, 2H), 3.07 (d, J=13.2 Hz, 1H), 2.91 (b, 2H), 2.66 (d, J=7.2 Hz, 2H), 2.49–2.44 (m, 1H), 2.45 (d, J=13.2 Hz, 1H), 2.27–2.20 (m, 1H), 2.14–2.06 (m, 1H), 1.90–1.78 (m, 1H), 1.40–1.33 (m, 1H), 1.15 (s, 3H), 1.02 (d, J=6.4 Hz, 6H), 0.94 (d, J=6.4 Hz, 6H), 0.93 (s, 3H); $^{13}$C NMR (CDCl$_3$, 100.6 MHz) δ 171.0, 138.2, 130.1, 127.4, 126.7, 124.1, 119.4, 115.9, 81.6, 53.9, 51.0, 49.9, 46.9, 46.5, 46.4, 43.5, 26.0, 24.9, 22.4, 20.4, 20.0, 19.5; MS (EI) m/z (relative intensity) 490 (m$^+$+1, 4.52), 420 (54), 316 (55), 215 (32), 151 (71), 105 (100), 77 (68), 43 (29); HRMS cacld for C$_{27}$H$_{39}$NO$_5$S (M$^+$) m/z 489.2549, found 489.2556; Anal. Calcd for C$_{27}$H$_{39}$NO$_5$S: C, 66.23; H, 8.03; N, 2.82; S, 6.55. Found: C. 66.25; H, 8.08; N, 2.87; S, 6.53.

Example 5

Example 5 illustrates the alcoholysis of the alkylated 1,3-dioxolanones of formula IV to form α-hydroxy acids derivatives of formula VI and 10-camphorsulfonamide of formula I.

(2R)-Ethyl 2-Hydroxy-3-phenylproponate

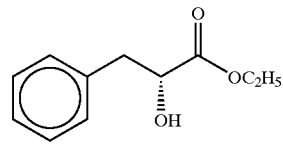

Anhydrous hydrogen chloride was bubbled through a solution of (1R,2S,5'R)-N,N-diisopropyl-[2-spiro-2'-(5'phenylmethyl-1',-3'-dioxolane-4'-one)-7,7-dimethylbicyclo[2.2.1]hept-1-yl]methanesulfonamide (464 mg, 1 mmol) in absolute ethanol (4 mL) for 10 min. After being refluxed for 6 hour, the solution was cooled, poured into the saturated NaHCO$_{3(aq)}$, and extracted twice with ether. The combined organic phases were washed with brine, dried (MgSO$_4$), and concentrated. The crude product was purified by column chromatography (SiO$_2$, hexane-EtOAc, 6:1) to give 161 mg(83%) of title compound and recover (1S)-(+)-N,N-diisopropyl-1-camphorsulfonamide (287 mg, 91%).

$[\alpha]_D^{25}$+22.21 (c 3.85, CHCl$_3$; IR (neat) 3471(b), 3085, 3060, 3030, 2982, 2939, 1733, 1604, 1497, 1455, 1370, 1201, 1096, 1031 cm$^{-1}$; $^1$H NMR (CDCl$_3$, 400 MHz) δ 7.19–7.30 (m, 5H), 4.42 (dd, J=6.4, J=4.4 Hz, 1H), 4.2 (quatet, J=7.2 Hz, 2H), 3.11 (dd, J=13.6, J=4.4 Hz, 1H), 2.95 (dd, J=13.6, J=6.4 Hz, 1H), 1.26 (t, J=7.2 Hz, 3H); $^{13}$C NMR (CDCl$_3$, 100.6 MHz) δ 174.1, 136.3, 129.4, 128.2, 126.7, 71.1, 61.5, 40.4, 14.0.

Example 6a–c

Examples 6a–c illustrate the hydrolysis of the alkylated 1,3-dioxolanones of formula IV to form α-hydroxy acids of formula V and 10-camphorsulfonamide of formula I. The general procedures of the hydrolysis are as follows: A solution containing 1 g of the alkylated 1,3-dioxolanones in 4 mL of methanol and 1 mL of 1N NaOH$_{(aq)}$ was heated at 60° C. for 4 h. After the solution was cooled, methanol was evaporated in vacuo. The residue was diluted with water (5 mL), and extracted with EtOAc (2×10 mL). The organic phases were dried (Na$_2$SO$_4$) and concentrated to recover 10-camphorsulfonamide. The pH value of aqueous layer was adjusted to 2 with concentrated HCl$_{(aq)}$, and then the solvent (water) was vaporized in reduced pressure. The residue was dissolved in 10 mL of ether and filtered to remove salt (NaCl). The resulting solution was dried with Na$_2$SO$_{4(s)}$ and concentrated to give the desired α-hydroxy acids.

Example 6a (2R)-2-Hydroxy-2-methylbutanoic Acid

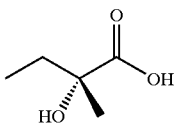

The title compound was prepared from the hydrolysis of (1R,2S,5'R)-N,N-diisopropyl-[2-spiro-2'-(5'-ethyl-5'-methyl-1',-3'-dioxolane-4'-one)-7,7-dimethylbicyclo[2.2.1]hept-1-yl]methanesulfonamide.

97% Yield of the title compound; and 96% recovery yield of (1S)-(+)-N,N-diisopropyl-10-camphorsulfonamide; mp=72.4–72.6° C.; $[\alpha]_D^{24}$–7.03 (c 1.4, 0.2N NaOH); IR (KBr) 3447, 3343, 2981–2583 (b), 1737 cm$^{-1}$; $^1$H NMR (CDCl$_3$, 400 MHz) δ 7.02 (b, 1H), 1.84–1.66 (m, 2H), 1.43 (s, 3H), 0.90 (t, J=7.3 Hz, 3H); $^{13}$C NMR (CDCl$_3$, 100.6 MHz) δ 181.8, 75.2, 32.9, 25.4, 7.8; MS (EI) m/z (relative intensity) 118 (M+, 2), 73 (100), 71 (14), 57 (42), 55 (90).

Example 6b (2R)-2-Hydroxy-2-methylhexanoic Acid

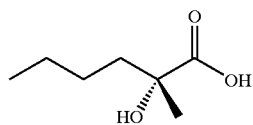

The title compound was prepared from the hydrolysis of (1R,2S,5'R)-N,N-Diisopropyl-(2-spiro-2'-(5'-methyl-5'-butyl-1',3'-dioxolane-4'-one)-7,7-dimethylbicyclo[2.2.1]hept-1-yl]methanesulfonamide.

98% Yield of title compound; and 92% recovery yield of (1S)-(+)-N,N-diisopropyl-10-camphorsulfonamide; mp=67.8–67.9° C.; $[\alpha]_D^{23}$–8.12 (c 0.85, H$_2$O); IR (neat) 3457, 3421, 2961–2578(b), 1735 cm$^{-1}$; $^1$H NMR (CDCl$_3$, 400 MHz) δ 7.10 (b, 1H), 1.78–1.62 (m, 2H), 1.43 (s, 3H), 1.31–1.13 (m, 4H), 0.86 (t, J=6.96 Hz, 3H); $^{13}$C NMP, (CDCl$_3$, 100.6 MHz) δ 161.8, 74.9, 39.7, 25.8, 25.7, 22.7, 13.8; MS (EI) m/z (relative intensity) 146 (M+, 39.51), 128 (44), 122 (42), 85 (59), 55 (100).

Example 6c (2S)-2-Hydroxy-2-phenyl-4-pentenoic Acid

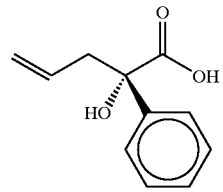

The title compound was prepared from the hydrolysis of (1R,2S,5'S)-N,N-Diisopropyl-{2-spiro-2'-(5'-phenyl-5'-(prop-2"-enyl)-1',3'-dioxolane-4'-one)-7,7-dimethylbicyclo[2.2.1]hept-1-yl}methanesulfonamide.

94% Yield of the title compound, and 93% recovery yield of (1S)-(+)-N,N-diisopropyl-10-camphorsulfonamide; mp=132.1–132.3° C.; $[\alpha]_D^{26}$+29.54 (c 1.0, CHCl$_3$); IR (neat) 3423, 3080, 2915, 1725, 1640 cm$^{-1}$; $^1$H NMR (CDCl$_3$, 400 MHz) δ 7.61–7.60 (m, 2H), 7.37–7.24 (m, 3H), 5.81–5.71 (m, 2H), 5.25–5.81 (m, 2H), 3.02 (dd J=14, J=7.2 Hz, 1H), 2.79 (dd, J=14, J=7.2 Hz, 1H); $^{13}$C NMR (CDCl$_3$, 100.6 MHz) δ 178.5, 140.2, 131.7, 128.4, 128.2, 125.5, 120.4, 77.8, 44.1.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A process for preparing α-hydroxy acids and derivatives thereof, comprising the step of subjecting the alkylated 1,3-dioxolanones of formula IV

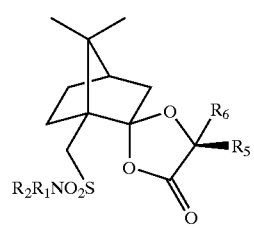

IV wherein R$_1$ and R$_2$ are the same or different and are each independently H or C$_{1-6}$ alkyl; R$_5$ is H, C$_{1-16}$ alkyl, or unsubstituted or substituted phenyl; and R$_6$ is C$_{1-8}$ alkyl, C$_{2-7}$ alkenyl or unsubstituted or substituted benzyl, to either (i) alcoholysis, when R$_5$ is H, to form α-hydroxy acids derivatives of formula V

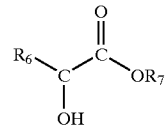

V wherein R₆ is $C_{1-8}$ alkyl, $C_{2-7}$ alkenyl or unsubstituted or substituted benzyl, and R₇ is $C_{1-6}$ alkyl, and isolating the resulting product; or (ii) hydrolysis, when R₅ is $C_{1-16}$ alkyl or unsubstituted or substituted phenyl, to form α-hydroxy acids of formula VI

VI wherein R₅ is H, $C_{1-16}$ alkyl, or unsubstituted or substituted phenyl; and R₆ is $C_{1-8}$ alkyl, $C_{2-7}$ alkenyl or unsubstituted or substituted benzyl, and isolating the resulting products (V) and (VI).

2. The process of claim 1, which additionally comprises the step of producing the alkylated 1,3-dioxolanones of formula IV

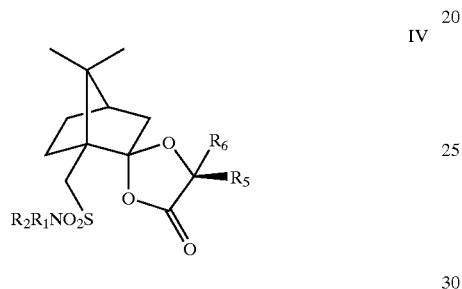

IV wherein R₁ and R₂ are the same or different and are each independently H or $C_{1-6}$ alkyl; R₅ is H, $C_{1-16}$ alkyl, or unsubstituted or substituted phenyl; and R₆ is $C_{1-8}$ alkyl, $C_{2-7}$ alkenyl or unsubstituted or substituted benzyl, by reacting the 1,3-dioxolanones of formula III

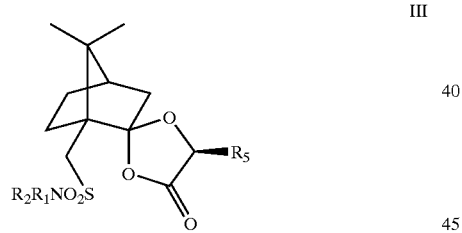

III wherein R₁ and R₂ are the same or different and are each independently H or $C_{1-6}$ alkyl, and R₅ is H, $C_{1-16}$ alkyl, or unsubstituted or substituted phenyl, with alkylation reagents of R₆X, wherein R₆ is $C_{1-8}$ alkyl, $C_{2-7}$ alkenyl or unsubstituted or substituted benzyl, and X is a leaving group, and isolating the resulting products (IV).

3. The process of claim 2, which additionally comprises the step of producing the 1,3-dioxolanones of formula III

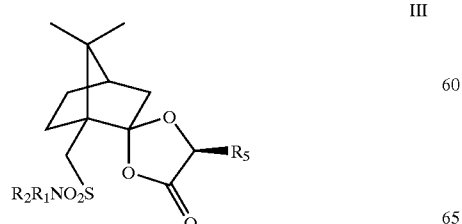

III wherein R₁ and R₂ are the same or different and are each independently H or $C_{1-6}$ alkyl, and R₅ is H, $C_{1-16}$ alkyl, or unsubstituted or substituted phenyl, by reacting the dialkoxy acetal of formula II

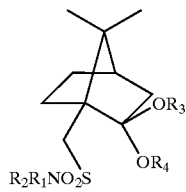

II wherein R₁ and R₂ are the same or different and are each independently H or $C_{1-6}$ alkyl, and R₃ and R₄ are the same or different and are each independently $C_{1-4}$ alkyl; with an α-hydroxy acid having the formula

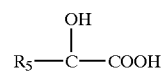

wherein R₅ is H, $C_{1-16}$ alkyl, or unsubstituted or substituted phenyl, and isolating the resulting products (III).

4. The process of claim 3, which additionally comprises the step of producing the dialkoxy acetal of formula II

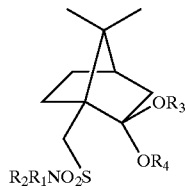

II wherein R₁ and R₂ are the same or different and are each independently H or $C_{1-6}$ alkyl, and R₃ and R₄ are the same or different and are each independently $C_{1-4}$ alkyl; by reacting the 10-camphorsulfonamide of formula I

I wherein R₁ and R₂ are the same or different and are each independently H or $C_{1-6}$ alkyl, with alkoxy-substituted alkane, and isolating the resulting products (II).

5. The process of claim 1, wherein the 10-camphorsulfonamide of formula I

I wherein R₁ and R₂ are the same or different and are each independently H or $C_{1-6}$ alkyl, is produced as a product and is recovered.

6. The process of claim 2, wherein the by-product of the 1,3-dioxolanone of formula IIIa is produced

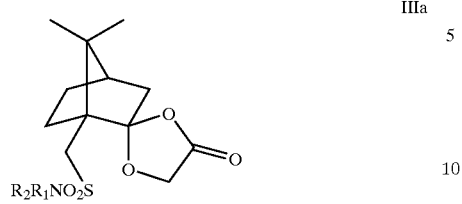

IIIa wherein $R_1$ and $R_2$ are the same or different and are each independently H or $C_{1-6}$ alkyl, and then isolated.

7. The process of claim 1, wherein the product is selected from the group consisting of (2R)-ethyl 2-hydroxy-3-phenylproponate, (2R)-2-hydroxy-2-methylbutanoic acid, (2R)-2-hydroxy-2-methylhexanoic acid, and (2S)-2-hydroxy-2-phenyl-4-pentenoic acid.

8. The process of claim 2, wherein the alkylated 1,3-dioxolanones of formula IV are selected from the group consisting of (1R,2S,5+R)-N,N-diisopropyl-[2-spiro-2'-(5'-methyl-1'-3'-dioxolane-4'-one)-7,7-dimethylbicyclo [2.2.1] hept-1-yl]methanesulfonamide, (1R,2S,5'S)-N,N-diisopropyl-{2-spiro-2'-[5'-(prop-2"-enyl)-1',-3'-dioxolane-4'-one]-7,7-dimethylbicyclo[2.2.1]hept-1-yl}methanesulfonamide, (1R,2S,5'R)-N,-diisopropyl-[2-spiro-2'-(5'-ethyl-1',-3'-dioxolane-4'-one)-7,7-dimethylbicyclo[2.2.1]hept-1-yl]methanesulfonamide, (1R,2S,5'R)-N,N-diisopropyl-[2-spiro-2'-(5'phenylmethyl-1',-3'-dioxolane-4'-one)-7,7-dimethylbicyclo[2.2.1]hept-1-yl]methane sulfonamide, (1R,2S,5'R)-N,N-diisopropyl-[2-spiro-2'-(5'-ethyl-5'-methyl-1',-3'-dioxolane-4'-one)-7,7-dimethylbicyclo[2.2.1]hept-1-yl]methanesulfonamide, (1R,2S,5'R)-N,N-diisopropyl-{2-spiro-2'-(5'-methyl-5'-propyl-1',3'-dioxolane-4'-one)-7,7-dimethylbicyclo[2.2.1]hept-1-yl}methanesulfonamide, (1R,2S,5'R)-N,N-diisopropyl-{2-spiro-2'-[5'-methyl-5'-(prop-2"-enyl)-1',3'-dioxolane-4'-one]-7,7-dimethylbicyclo[2.2.1]hept-1-yl}methanesulfonamide, (1R,2S,5'R)-N,N-diisopropyl-[2-spiro-2'-(5'-methyl-5'-butyl-1',3'-dioxolane-4'-one)-7,7-dimethylbicyclo[2.2.1]hept-1-yl]methanesulfonamide, (1R,2S,5'R)-N,N-diisopropyl-[2-spiro-2'-(5'-methyl-5'-phenylmethyl-1',3'-dioxolane-4'-one)-7,7-dimethylbicyclo[2.2.1]hept-1-yl]methane sulfonamide, (1R,2S,5'S)-N,N-diisopropyl-[2-spiro-2'-(5'-methyl-5'-phenyl-1',3'-dioxolane-4'-one)-7,7-dimethylbicyclo[2.2.1]hept-1-yl]methanesulfonamide, and (1R,2S,5'S)-N,N-diisopropyl-{2-spiro-2'-(5'-phenyl-5'-(prop-2"-enyl)-1',3'-dioxolane-4'-one)-7,7-dimethylbicyclo[2.2.1]hept-1-yl}methanesulfonamide.

9. The process of claim 3, wherein the 1,3-dioxolanones of formula III is selected from the group consisting of (1R,2S)-N,N-diisopropyl-[2-spiro-2'-(1'-3'-dioxolane-4'-one)-7,7-dimethylbicyclo[2.2.1 ]hept-1-yl] methanesulfonamide, (1R,2S,5'S)-N,N-diisopropyl-[2-spiro-2'-(5'-methyl-1',3'-dioxolane-4'-one)-7,7-dimethylbicyclo[2.2.1]hept-1-yl]methanesulfonamide, and (1R,2S,5'S)-N,N-diisopropyl-[2-spiro-2'-(5'-phenyl-1',3'-dioxolane-4'-one)-7,7-dimethylbicyclo[2.2.1]hept-1-yl] methanesulonamide.

10. The proccess of claim 4, wherein the dialkoxy acetal of formula II is (1R)-N,N-diisopropyl-(2,2-dimethoxy-7,7-dimethylbicyclo[2.2.1]hept-1-yl)methanesulfonamide.

11. The process of claim 2, wherein the reaction is conducted under the temperature in the range of −100° C. to −45° C.

12. A process for preparing optically active α-hydroxy acids, comprising steps (a) reacting 10-camphorsulfonamide of formula I

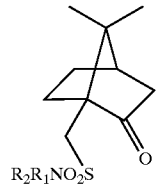

I wherein $R_1$ and $R_2$ are the same or different and are each independently H or $C_{1-6}$ alkyl,
with alkoxy-substituted alkane in the presence of an alcohol and p-toluene sulfonic acid to form dialkoxy acetal of formula II

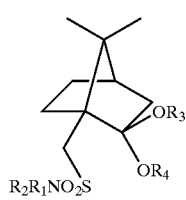

II wherein $R_1$ and $R_2$ are the same or different and are each independently H or $C_{1-6}$ alkyl, and $R_3$ and $R_4$ are the same or different and are each independently $C_{1-4}$ alkyl;

(b) reacting the dialkoxy acetal of formula II with an α-hydroxy acid having the formula

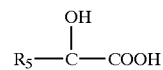

wherein $R_5$ is H, $C_{1-16}$ alkyl, or unsubstituted or substituted phenyl, in the presence of an ether and a Lewis acid to form the 1,3-dioxolanones of formula III

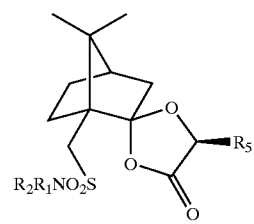

III wherein $R_1$ and $R_2$ are the same or different and are each independently H or $C_{1-6}$ alkyl, and $R_5$ is H, $C_{1-16}$ alkyl, or unsubstituted or substituted phenyl;

(c) reacting the 1,3-dioxolanones of formula III with alkylation reagents in the presence of a strong base and optionally of hexamethyl phosphoramide under the temperature in the range between −100° C. to 0° C. to form the alkylated 1,3-dioxolanones of formula IV

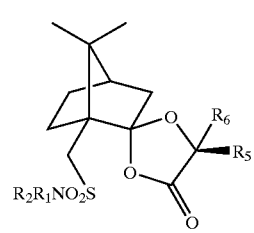

IV wherein $R_1$ and $R_2$ are the same or different and are each independently H or $C_{1-6}$ alkyl, $R_5$ is H, $C_{1-6}$ alkyl, or unsubstituted or substituted phenyl, and $R_6$ is $C_{1-8}$ alkyl, $C_{2-7}$ alkenyl or unsubstituted or substituted benzyl;

(d) subjecting the alkylated, 1,3-dioxolanones of formula IV to either (i) alcoholysis, when $R_5$ is H, to form α-hydroxy acids derivatives of formula V

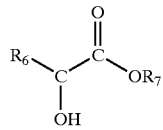

V wherein $R_6$ is $C_{1-8}$ alkyl, $C_{2-7}$ alkenyl or unsubstituted or substituted benzyl, and $R_7$ is $C_{1-6}$ alkyl, or (ii) hydrolysis, when $R_5$ is $C_{1-16}$ alkyl or unsubstituted or substituted phenyl, to form α-hydroxy acids of formula VI

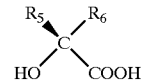

VI wherein $R_5$ is H, $C_{1-16}$ alkyl, or unsubstituted or substituted phenyl, and $R_6$ is $C_{1-8}$ alkyl, $C_{2-7}$ alkenyl or unsubstituted or substituted benzyl, and recovering the 10-camphorsulfonamide of formula I.

* * * * *